United States Patent [19]

Komai et al.

[11] Patent Number: 4,929,747

[45] Date of Patent: May 29, 1990

[54] ORGANIC PEROXIDE HAVING A POLYMERIZATION-REGULATING ABILITY

[75] Inventors: Takeshi Komai, Chita; Kazuo Matsuyama, Gamagori; Isao Honma, Chita, all of Japan

[73] Assignee: Nippon Oil & Fats Company, Ltd., Japan

[21] Appl. No.: 895,995

[22] Filed: Aug. 13, 1986

[30] Foreign Application Priority Data

Aug. 21, 1985 [JP] Japan .................................. 60-181623
Aug. 21, 1985 [JP] Japan .................................. 60-181624

[51] Int. Cl.$^5$ ............................................. C07C 179/18
[52] U.S. Cl. .................................. 558/263; 526/230.5
[58] Field of Search .......................................... 558/263

[56] References Cited

U.S. PATENT DOCUMENTS 4,526,726 7/1985 Tang .................................... 558/263

FOREIGN PATENT DOCUMENTS 1301533 8/1969 Fed. Rep. of Germany .
2528492 1/1976 Fed. Rep. of Germany .

OTHER PUBLICATIONS

Schwartz et al., J. Amer. Chem. Society, 99:8, Apr. 13, 1977, pp. 2571-2578.
Chemical Abstracts, vol. 87, 1977, p. 644, 87:200543n.
Chemical Abstracts, vol. 90, 1979, p. 594, 90:168504z.
Bourgeois et al., "Synthesis and Reactivity of Tert-Butyl Imidazolylpercarboxylate", Tetrahedron Letters No. 36, pp. 3355-3358, 1978.
Minns, "2-Troponyl and Phenyl Tert-Butylperoxycarbonates," 1976, (Dissertation and Abstract).
Razuvaev et al., "Perbenzoylalkyl(aryl) Carbonates," Bulletin of Academy of Science USSR, pp. 400-403, 1982.

*Primary Examiner*—Vivian Garner
*Attorney, Agent, or Firm*—Arnold, White & Durkee

[57] ABSTRACT

A novel peroxy aryl carbonate which has the both properties of polymerization-initiating and regulating abilities, can be used as a radical polymerization initiator to regulate the polymerization rate, the polymerization degree and molecular weight distribution of the polymer and the like, and therefore produce superior styrene resin and methyl methacrylate syrup.

4 Claims, 4 Drawing Sheets

FIG_1

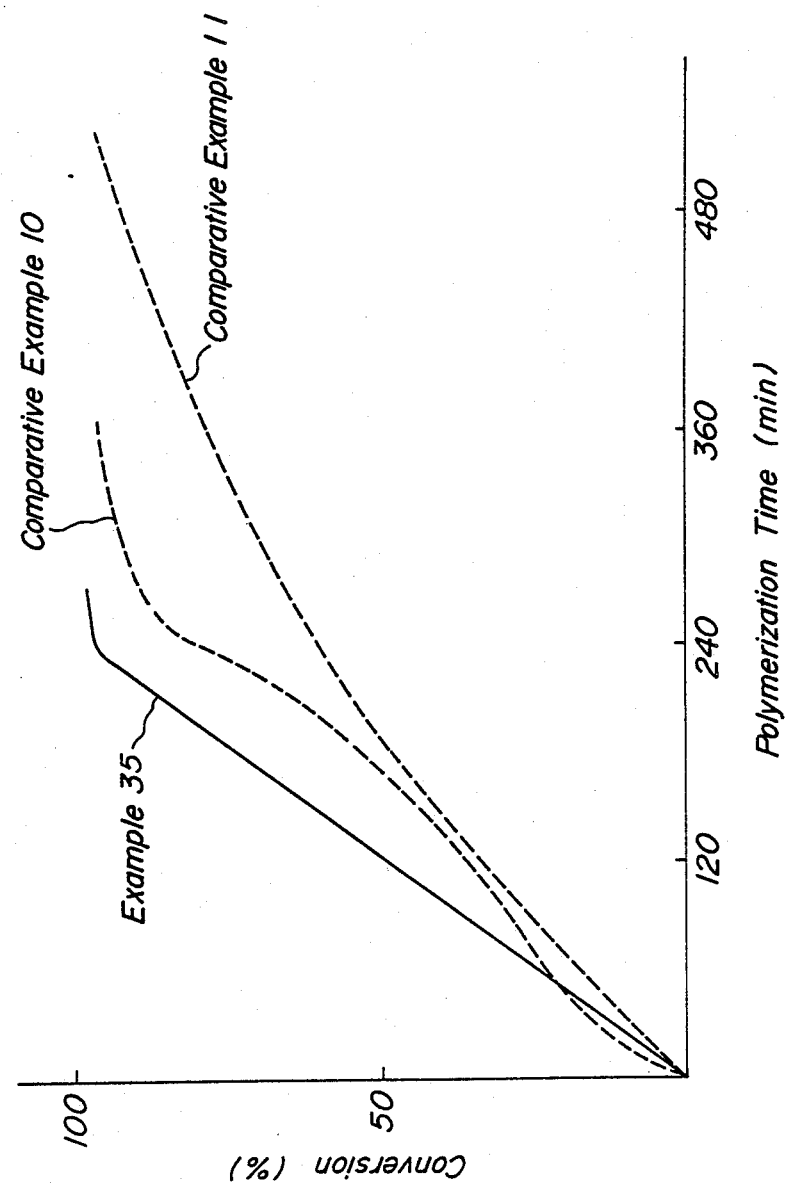

FIG_4
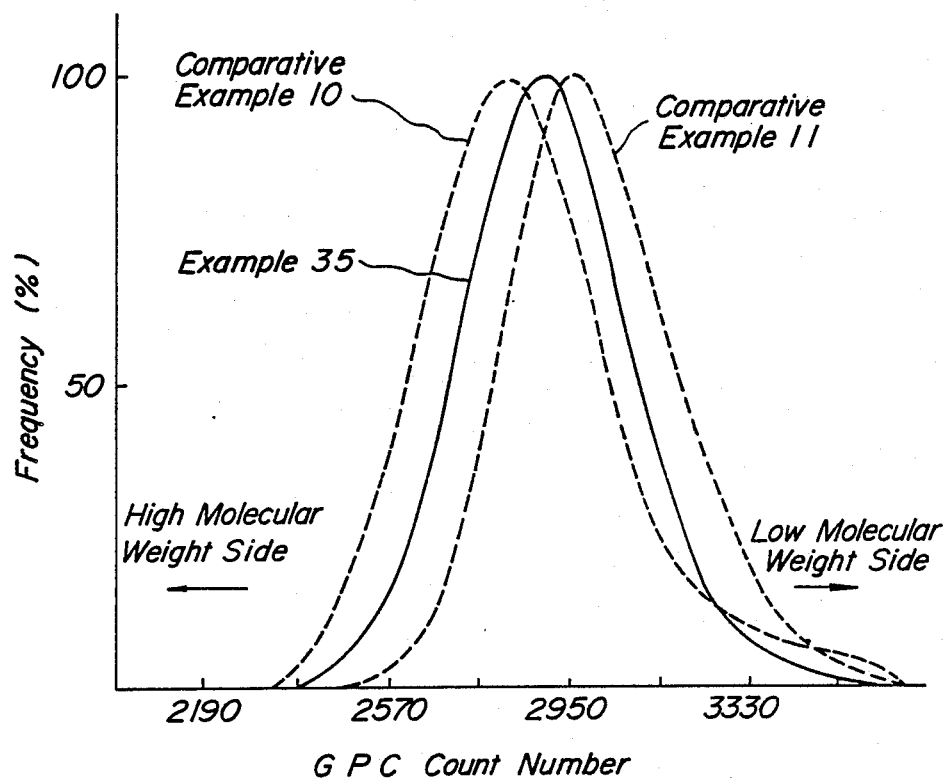

ORGANIC PEROXIDE HAVING A POLYMERIZATION-REGULATING ABILITY

BACKGROUND OF THE INVENTION

1. Field of the Invention

The present invention relates to an organic peroxide having a polymerization-regulating ability, and more particularly relates to a peroxy aryl carbonate having a polymerization-regulating ability in the radical polymerization or copolymerization reaction of unsaturated monomers and further having a polymerization-initiating ability for the reaction.

2. Description of the Related Art Statement

There are various factors, such as polymerization rate, polymerization degree and molecular weight distribution of the resulting polymer and the like, in the polymerization regulation. In the radical polymerization or copolymerization of unsaturated monomers, these factors have an intimate relation to the polymerization heat, and the flowability, workability and mechanical property of the resulting polymer The regulation of polymerization is the most important problem in the field of polymer chemistry, particularly in the industrial field of polymer chemistry at present.

In general, the reciprocal of the number-average average polymerization degree $\bar{P}_n$ of a polymer formed in the initial stage of a radical polymerization of unsaturated monomers, and the polymerization rate are represented, as described on pages 387–388 in "Shin Jikken Kagaku Koza, Vol. 19, Kōbunshi Kagaku [I]" edited by the Chemical Society of Japan and published by Maruzen (1975), by the following formulae (1) and (2):

$$\frac{1}{\bar{P}_n} = \frac{k_{trM}}{k_p} + \frac{k_{trI}[I]}{k_p[M]} + \frac{k_{trA}[A]}{k_p[M]} + \frac{(1+x)\bar{k}_t R_p}{k_p^2[M]^2} \quad (1)$$

$$R_p = \left(\frac{2fk_d k_p^2}{k_t}\right)^{\frac{1}{2}} [M][I]^{\frac{1}{2}} \quad (2)$$

(in the formulae (1) and (2), $k_{trM}$, $k_{trI}$ and $k_{trA}$ represent the rate constants of chain transfer of polymer radical into the unsaturated monomer, polymerization initiator and polymerization regulator, respectively; $\bar{k}_t$ and $k_p$ represent the rate constants of termination reaction and propagation, respectively; $k_d$ and f represent the decomposition rate constant of polymerization initiator and the initiator efficiency, respectively; [I], [M] and [A] represent the concentrations of polymerization initiator, unsaturated monomer and polymerization regulator, respectively; $R_p$ represents the polymerization rate; and X represents the ratio of disproportional termination reaction.)

In the formula (1) the first second and third terms of the right side are terms based on the chain transfer reactions of the polymer radical to the unsaturated monomer, polymerization initiator and polymerization regulator, respectively; and the fourth term of the right side is a term based on the termination reaction between polymer radicals.

According to the formula (1), the polymerization degree decreases with the increase of the polymerization concentration of the polymerization regulator. Accordingly, the polymerization degree of a polymer to be formed is generally regulated by changing the polymerization rate or by adding to the polymerization system a polymerization regulator having a known chain transfer constant represented by $k_{trA}/k_p$.

For example, the above described publication describes that the formula (1) is established in the polymerization of styrene initiated by azoisobutyronitrile and dibenzoyl peroxide. Japanese Patent Application Publication No. 10,046/59 discloses that the polymerization rate is increased with increasing the concentration of dibenzoyl peroxide, and polymers having various polymerization degrees can be obtained.

Japanese Patent Laid-open Application No. 52,886/73 discloses that, when alkyl mercaptan and carbon tetrabromide are used, the polymerization degree of the resulting polymer is decreased and the polymer solution has a very low relative viscosity.

Belgian Pat. No. 660383 discloses that a peroxy carbonate represented by the following genera formula (II)

$$R-O-O-\overset{\overset{\displaystyle O}{\|}}{C}-O-R' \quad (II)$$

wherein R represents a tert-alkyl group or a tert-aralkyl group; and R' represents an alkyl group, an aralkyl group, an aryl group or an alkoxyalkyl group, can be utilized as a polymerization initiator for unsaturated monomer.

The polymerization-regulating technique which uses conventional polymerization initiator and polymerization regulator has several drawbacks, which are as follows.

That is, when the polymerization rate is higher, the control of the polymerization reaction becomes very difficult due to the increase of polymerization heat and to the rapid increase of viscosity in the polymerization system. For example, in the production of methyl methacrylate resin sheet, a syrup is used in order to suppress the heat generation due to polymerization or to prevent the shrinkage of the resulting polymer. In this case, the use of a syrup having a proper viscosity and having a high polymer content is desired. However, the use of an ordinary polymerization initiator causes difficulties in the control of polymerization reaction, and the resulting syrup has often an extraordinarily high viscosity.

In the recent production of styrene resin, the styrene resin is demanded to have excellent formability due to the development of a precise and high-speedy injection molding machine. However, it is generally difficult to produce a polymer having excellent formability due to the formation of a polymer having a very high molecular weight by the gel effect during the latter stage of the polymerization reaction. Further, when the polymerization initiator is used in a larger amount in order to lower the molecular weight of the resulting polymer, the resulting polymer has a poor mechanical property due to the formation of low molecular weight polymer. Therefore, it is a very important problem to produce a polymer having a uniform molecular weight.

In the above described method for producing a polymer by the use of carbon tetrabromide, the resulting polymer is poor in the thermal stability, and hence the polymer colors and decomposes noticeably at its processing temperature and is poor in the practical value of the formed article. Further, in the above described method for producing a polymer by the use of an alkyl mercaptan, it is known that the unpleasant odor of the alkyl mercaptan causes serious troubles in the use, and further unreacted alkyl mercaptan remaining in the resulting polymer affects adversely on the polymer. In the peroxy carbonate represented by the above described general formula (11), an isopropyl group, benzyl group, cycloalkyl group or the like is used as R'. However, the peroxy carbonate having such group is very poor in the polymerization-regulating ability.

SUMMARY OF THE INVENTION

The present invention provides an organic peroxide and a process free from the above described drawbacks.

That is, the feature of the present invention lies in an organic peroxide having a polymerization-regulating ability, that is, a peroxy aryl carbonate, represented by the following genera formula (I)

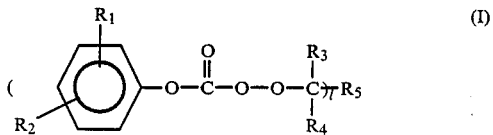

wherein, $R_1$ and $R_2$ represent hydrogen atoms, halogen atoms, or same or different alkyl groups having 1–10 carbon atoms, aralkyl groups having 7–12 carbon atoms, cycloalkyl groups having 5–8 carbon atoms, alkoxy groups having 1–4 carbon atoms, or acyl groups having 1–6 carbon atoms; $R_3$ and $R_4$ represent same or different lower alkyl groups having 1–4 carbon atoms; and $R_5$ represents an alkyl group having 1–12 carbon atoms or a cycloalkyl group having 3–12 carbon atoms in the case of $l=1$, or a —C≡C— group or group-$(CH_2)_m$ is an integer of 2-4) in the case of $l=2$.

BRIEF DESCRIPTION OF THE DRAWINGS

FIGS. 1 and 3 are graphs illustrating relations between the conversion and the polymerization time in Example 34 and Comparative examples 8 and 9, and in Example 35 and Comparative examples 10 and 11, respectively, in this specification; and FIGS. 2 and 4 are gel permeation chromatography (abbreviated as GPC) curves of polymers obtained in Example 34 and Comparative examples 8 and 9, and in Example 35 and Comparative examples 10 and 11, respectively, in this specification.

Figure 1:
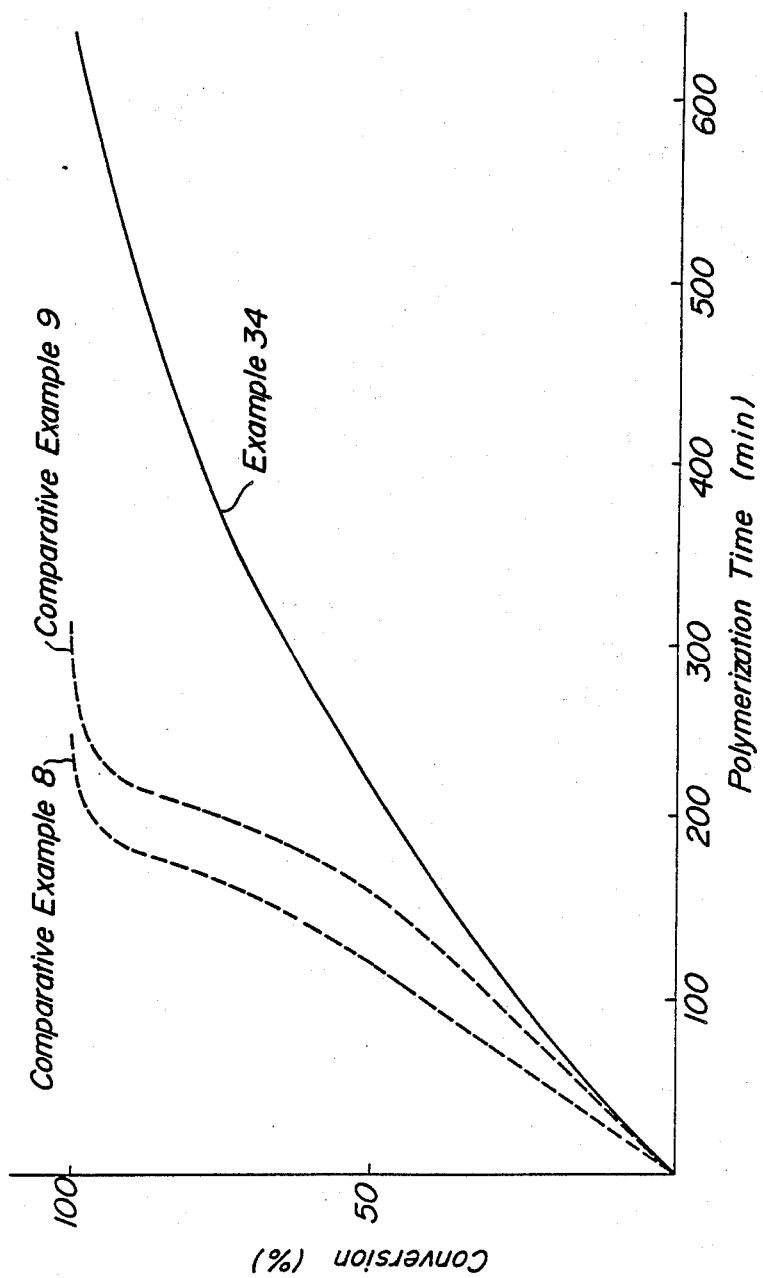

In all the figures, the solid line represents example, and the broken line represents comparative example.

DESCRIPTION OF THE PREFERRED EMBODIMENT

The inventors have found that the organic peroxide of the present invention can be produced by a conventional method, and that, when a polymerization reaction of an unsaturated monomer is carried out by the use of this peroxy aryl carbonate as a polymerization initiator, a polymer having a polymerization degree, which is remarkably lower than a polymer obtained by the use of the conventional polymerization initiator, can be obtained at the same polymerization rate, and hence that the peroxy aryl carbonate is effective for controlling the polymerization.

The organic peroxides of the present invention include carbonates of a hydroperoxide such as tert-butyl hydroperoxide, tert-amyl hydroperoxide, tert-hexyl hydroperoxide or 1,1,3,3-tetramethylbutyl hydroperoxide, with phenol or a phenol derivative such as 2-methylphenol, 3-methylphenol, 2,4-dimethylphenol 2,6-dimethylphenol, 2-isopropylphenol, 2-sec-butylphenol, 4-tertbutylphenol, 4-(1,1,3,3-tetramethylbutyl)-phenol, 4-cumylphenol, 2-cyclohexylphenol, 2-chlorophenol, 3-chlorophenol, 4-chlorophenol, 2,4-dichlorophenol, 2-bromophenol, 3-bromophenol, 2,6-dibromophenol, 3-methoxyphenol, 4-methoxyphenol, 4-ethoxyphenol, 4-acetylphenol, 2-chloro-4-methylphenol, 2-bromo-4-methylphenol, 3-methyl-4-bromophenol or 2-methyl-4-acetylphenol, 2,5-dimethyl-2,5-di(phenoxycarbonylperoxy)hexane, 2,5-dimethyl-2,5-di(4-methylphenoxycarbonylperoxy)hexane, 2,5-dimethyl-2,5-di(4-chlorophenoxycarbonylperoxy)hexane, 2,5-dimethyl-2,5-di(phenoxycarbonylperoxy)hexyne and the like. These peroxy aryl carbonates are generally colorless liquids or white crystals and are odorless. Concrete properties of these carbonates are illustrated in the Examples. These carbonates are selected from the viewpoint of both the polymerization-regulating ability of the carbonate itself and the easiness in obtaining the raw materials for the production of the carbonates.

The organic peroxide can be obtained by reacting an aryl chloroformate represented by the following general formula (III)

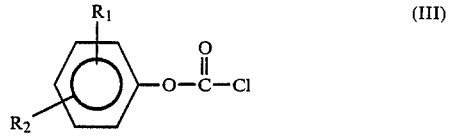

Wherein $R_1$ and $R_2$ have the same meanings as those in the above described general formula (I), with a tert-alkyl hydroperoxide represented by the following general formula (IV)

wherein $R_3$, $R_4$, $R_5$ and $l$ have the same meanings as those in the above described general formula (I), at a temperature of from $-30°$ C. to $30'°$ C. in the presence of an alkali or tert-amine. However, the tert-aralkylperoxy aryl carbonate, which is included with the scope of the peroxy carbonates represented by the general formula (II) in the above described Belgian Pat. No. 660383 and corresponds to the case where R represents a tert-aralkyl group and R' represents an aryl group in the general formula (II), has a peculiar reactivity, and can not be produced according to the above described method.

The chemical structure of the organic peroxide of the present invention can be determined by the infrared absorption spectrum and nuclear magnetic resonance spectrum, the purity thereof can be determined by the gas-liquid chromatography (GLC) and by the amount of active oxygens, and the thermal decomposition behavior thereof can be determined by the decomposition rate constant and half-life period. The organic peroxide of the present invention has a half-life period within the range of 1–20 hours at 100° C. and is a peroxide having an intermediate- or high-temperature activity, which exhibits substantially the same decomposition activity as that of a conventional polymerization initiator such as t-butylperoxy isopropyl carbonate. Most of the organic peroxide of the present invention is poor in safety and decomposes explosively such as other peroxides. However, the organic peroxides can be used in a stable form, that is, in a diluted state with an organic solvent, in a hydrated state, in a water-emulsion state or in a water-suspension state.

The organic peroxide and the process of the present invention are useful for a radical polymerization or copolymerization of unsaturated monomers and exhibit polymerization-regulating ability. The unsaturated monomers include radically polymerizable or copolymerizable vinyl-type and ethylene-type unsaturated monomers, such as ethylene, vinyl chloride, vinyl acetate, acrylonitrile, vinylidene chloride, acrylic acid ester, methacrylic acid ester, fumaric acid ester, styrene and the like.

The organic peroxide of the present invention is used in an amount of 0.00005–0.2 mole based on 1 mole of the unsaturated monomer, and can be used for the production of various polymers ranging from a low molecular weight polymer called as oligomer to a high molecular weight polymer called as plastics, in the process of the present invention. When the use amount is less than the lower limit of the above described range, the organic peroxide can not exhibit fully its effect, and even when the use amount is larger than the upper limit of the above described range, the organic peroxide does not show a remarkable effect, and furthermore the use of an excessively large amount of the organic peroxide is not economic.

The polymerization or copolymerization of the unsaturated monomers in the process of the present invention can be carried out by any of vinyl polymerization methods known at present using a radical polymerization initiator, that is, by any of bulk polymerization method, solution polymerization method and aqueous medium polymerization method. In these polymerization methods, the organic peroxide of the present invention can be used in combination with one or more of other polymerization initiator, polymerization regulator and other polymerization additives.

The organic peroxide and the process of the present invention exhibit a behavior considerably different from that in the use of a conventional polymerization initiator which satisfies the above described formula (2) of polymerization rate.

That is, when the organic peroxide of the present invention is used as a polymerization initiator, a polymer having a polymerization degree considerably lower than that of a polymer obtained by the use of a conventional polymerization initiator can be obtained at the same polymerization rate. The polymerization reaction mechanism in the use of the polymerization initiator of the present invention is probably as follows. When the peroxy aryl carbonate of the organic peroxide of the present invention is thermally decomposed, cleavage of —O—O— bond occurs first according to the following formula (3) to form two kinds of active radicals, which act to initiate polymerizations of unsaturated monomers.

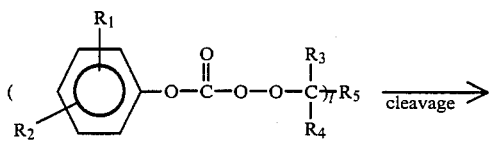
(3)

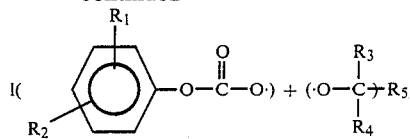

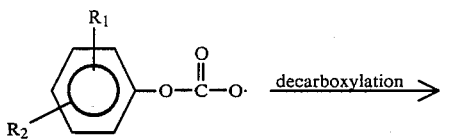

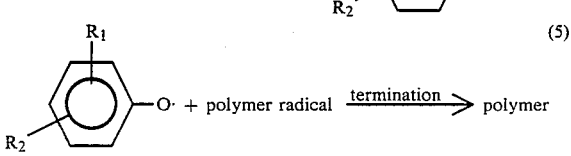

In the above described formula, l, $R_1$, $R_2$, $R_3$, $R_4$ and $R_5$ have the same meanings as described in the above described general formula (1).

Following to the above described cleavage of the —O—O— bond, a decarboxylation reaction occurs according to the formula (4) to form an inert radical, which is so stable not to initiate a polymerization reaction. The use of a conventional polymerization initiator does not form such inert radical, and therefore the chain reaction terminates due to the termination reaction between polymer radicals. However, when the above described inert radical is present in the polymerization system, the inert radical reacts with a polymer radical according to the formula (5) to terminate the chain reaction. Accordingly, the organic peroxide of the present invention probably exhibits a polymerization-regulating ability contrary to the conventional termination reaction between polymer radicals.

The organic peroxide of the present invention has a polymerization-regulating ability due to the above described particular action, and hence the organic peroxide and the process have the following various merits. First, when a polymerization reaction is carried out at the same polymerization rate as that in the use of a conventional polymerization initiator, a polymer having a molecular weight lower than that in the use of the conventional polymerization initiator can be obtained. Second, even when the polymerization system becomes high viscous, the polymerization rate does not increase abruptly and the gel effect can be prevented. Third, as the result of the effect of the second merit, the finally obtained polymer is uniform in the molecular weight distribution, and is small in the dispersion index. Fourth, the organic peroxide of the present invention has also a polymerization-initiating ability, and hence the use of the organic peroxide can shorten the time required for completing the polymerization reaction as compared with the use of a conventional polymerization regulator. Fifth, the organic peroxide of the present invention is odorless and can be easily handled.

These merits are concretely as follows. In the production of a styrene resin, when the organic peroxide of the present invention is used, gelatinization does not occur at the latter stage of the polymerization, and therefore the polymerization temperature can be easily controlled, and moreover the resulting styrene resin has a good formability due to its uniform molecular weight distribution. Moreover, when the organic peroxide of the present invention is used in combination with other polymerization initiator, the time required for completing the polymerization can be shortened.

Further, in the production of methyl methacrylate syrup, a syrup having a proper viscosity and a high polymer content can be stably produced, but the syrup is very low in the content of residual organic peroxide, which is a cause of gelatinization in the post stage of the polymerization. The organic peroxide of the present invention has the above described excellent properties, and hence the organic peroxide is used as an important polymerization modifier in the polymer chemical industry.

The present invention will be explained referring to the following Examples, Reference examples and Comparative examples, but is not limited to these examples.

(PRODUCTION OF ORGANIC PEROXIDE)

EXAMPLE 1

[Production of t-butylperoxy phenyl carbonate]

To 28.4 g (0.22 mol) of t-butyl hydroperoxide was added 200 g of petroleum ether, and after the separated water was removed, the resulting organic layer was dried with a small amount of magnesium sulfate. The resulting solution was charged into a four-necked flask of 500 ml capacity equipped with a thermometer and a stirrer, and 15.8 g (0.20 mol) of pyridine was added to the solution at 5° C. under stirring, and then 31.7 g (0.2 mol) of phenyl chloroformate was dropwise added to the mixture at 5° C. in 30 minutes under stirring. After completion of the addition, a reaction was further continued for 2 hours to complete the reaction.

The reaction solution was washed with 150 ml of a 5% aqueous solution of hydrochloric acid once at 5° C. for 5 minutes, with 100 ml of a 10% aqueous solution of sodium hyroxide once at 5° C. for 5 minutes, and with 150 ml of water twice, each at 10° C. for 5 minutes, and then dried with a small amount of sodium sulfate. The solvent was removed under reduced pressure from the dried solution to obtain 30.5 g (yield: 70%) of a crude product having a GLC (gas-liquid chromatography) purity of 94%. The crude product was recrystallized by using petroleum ether to obtain a white crystal having a melting point of 30° C., which had an active oxygen content of 7.51% theoretical value: 7.61%) and a GLC purity of 99%.

The resulting compound had an infrared absorption spectrum having characteristic absorption bands (in carbon tetrachloride solution) at 1,808 cm$^{-}$($v_{C=O}$), 1,780 cm$^{-1}$ ($v_{C=O}$), 1,600 cm$^{-1}$ (benzene ring) and 1,500 cm$^{-1}$ (benzene ring). When the chemical shift of proton in the nuclear magnetic resonance spectrum (in carbon tetrachloride solution) of the compound was represented by the δ value, the signal of proton of —C(CH$_3$) group appeared at a δ of 1.4 ppm (9H), and the signal of proton of benzene ring appeared at a δ of 7.3 ppm (5H). Therefore, the compound was identified to be t-butylperoxy phenyl carbonate.

EXAMPLE 2

[Production of t-butylperoxy phenyl carbonate]

A mixture of 48.0 g (0.30 mol) of phenyl chloroformate, 38.7 g (0.30 mol) of t-butyl hydroperoxide, 5.0 g of sodium chloride and 106.0 g of water was charged into a four-necked flask of 500 ml capacity equipped with a thermometer and a stirrer, and a 50% aqueous solution of sodium hydroxide was dropwise added to the mixture at a temperature of 2° C. in 25 minutes. After the addition, the reaction solution was kept at 10° C. for 1 hour to complete the reaction.

Water was separated from the reaction solution, and the obtained organic layer was washed at 20° C. with 30 g of a 10% aqueous solution of sodium hydroxide once and further with 30 g of a 10% aqueous solution of sodium sulfate twice, and then dried with a small amount of magnesium sulfate to obtain 40.3 g (yield: 58%) of t-butylperoxy phenyl carbonate having a GLC purity of 79%.

EXAMPLE 3

[Production of t-amylperoxy phenyl carbonate]

A reaction was carried out in the same manner as described in Example 1, except that t-amyl hydroperoxide was used in place of t-butyl hydroperoxide used in Example 1, to obtain 47.5 g (yield: 54%) of a crude product. The crude product was purified through a recrystallization by using methanol to obtain a colorless liquid at room temperature, which had an active oxygen content of 6.79% (theoretical value: 7.13%) and a GLC purity of 95%.

The resulting compound had an infrared absorption spectrum having characteristic absorption bands (in a liquid film) at 1,800 cm$^{-1}$ ($v_{C=O}$), 1,775 cm$^{-1}$ ($v_{C=O}$), 1,595 cm$^{-1}$ (benzene ring) and 1,495 cm$^{-1}$ (benzene ring). Further, when the chemical shift of proton in the nuclear magnetic resonance spectrum (in a deuterochloroform solution) of the compound was represented by the δ-value, the signal of proton of —CH$_2$CH$_3$ group appeared at a δ of 1.1 ppm (3H), that of proton of —C(CH$_3$)$_2$— group appeared at a δ of 1.3 ppm (6H), that of proton of —CH$_2$CH$_3$ group appeared at a δ of 1.7 ppm (2H) and that of proton of benzene ring appeared at a δ of 7.3 ppm (5H). Therefore, the compound was identified to be t-amylperoxy phenyl carbonate.

EXAMPLE 4

[Production of t-hexylperoxy phenyl carbonate]

Into a four-necked flask of 500 ml capacity equipped with a thermometer and a stirrer were charged 24.3 g (0.20 mol) of t-hexyl hydroperoxide, 15.8 g (0.20 mol) of pyridine and 200 g of petroleum ether, and then a mixture of 27.0 g (0.17 mol) of phenyl chloroformate and 30 g of petroleum ether was dropwise added thereto in 30 minutes while keeping the reaction system at 18° C. under stirring. After the addition, a reaction was further continued for 5 hours, and the precipitated pyridine hydrochloride salt was filtered off.

To the reaction solution were further added 1.0 g (0.013 mol) of pyridine and 7.0 g (0.058 mol) of phenyl chloroformate, and the reaction was further continued for 1 hour to complete the reaction. After completion of the reaction, the reaction solution was washed at 20° C. with 300 ml of water once, 300 ml of a 2% aqueous solution of sodium hydroxide once, and further 300 ml of water thrice, and then dried with a small amount of sodium sulfate. The solvent was removed from the reaction mass under reduced pressure to obtain 32.0 g (yield: 55%) of a compound which was a colorless liquid at room temperature and had a GLC purity of 94%.

The resulting compound had an infrared absorption spectrum having characteristic absorption bands (in a carbon tetrachloride solution) at 1,802 cm$^{-1}$ ($v_{C=O}$), 1,760 cm$^{-1}$ ($v_{C=O}$), 1,600 cm$^{-1}$ (benzene ring) and 1,500 cm$^{-1}$ (benzene ring). Further, when the chemical shift of proton in the nuclear magnetic resonance spectrum (in a deuterochloroform solution) of the compound was represented by the δ value, the signal of proton of —CH$_2$CH$_3$ group appeared at a δ of 0.9 ppm (5H), that of proton of —C(CH$_3$)$_2$— group appeared at a δ of 1.4 ppm (6H), that of proton of —C(CH$_3$)$_2$CH$_2$— group appeared at a δ of 1.7 ppm (2H) and that of proton of benzene ring appeared at a δ of 7.3 ppm (5H). Therefore, the compound was identified to be t-hexylperoxy phenyl carbonate.

EXAMPLE 5

[Production of t-butylperoxy 2-isopropylphenyl carbonate]

A reaction was carried out in the same manner as described in Example 1, except that 2-isopropylphenyl chloroformate was used in place of phenyl chloroformate used in Example 1, to obtain 30.9 g (yield: 54%) of a crude product having a GLC purity of 88%. The crude product was recrystallized by the use of methanol to obtain a compound having a GLC purity of 95%, which was a colorless liquid at room temperature.

The resulting compound had an infrared absorption spectrum having characteristic absorption bands (in a carbon tetrachloride solution) at 1,810 cm$^{-1}$ ($v_{C=O}$), 1,780 cm$^{-1}$ ($v_{C=O}$), 1,580 cm$^{-1}$ (benzene ring) and 1,500 cm$^{-1}$ (benzene ring). Further, when the chemical shift of proton in the nuclear magnetic resonance spectrum (in a carbon tetrachloride solution) of the compound was represented by the δ value, the signal of proton of —CH(CH$_3$)$_2$ group appeared at a δ of 1.2 ppm (6H), that of proton of —C(CH$_3$)$_3$ group appeared at a δ of 1.4 ppm (9H), that of proton of —CH(CH$_3$)$_2$ group appeared at a δ of 3.2 ppm (1H) and that of proton of benzene ring appeared at a δ of 7.3 ppm (4H). Therefore, the compound was identified to be t-butylperoxy 2-isopropylphenyl carbonate.

EXAMPLE 6

[Production of t-butylperoxy 2-sec-butylphenyl carbonate]

A reaction was carried out in the same manner as described in Example 1, except that 2-sec-butylphenyl chloroformate was used in place of phenyl chloroformate used in Example 1, to obtain 43.9 g (yield: 72%) of a compound having a GLC purity of 88%, which was a colorless liquid at room temperature.

The resulting compound had an infrared absorption spectrum having characteristic absorption bands (in a carbon tetrachloride solution) at 1,807 cm$^{-1}$ ($v_{C=O}$), 1,772 cm$^{-1}$ ($v_{C=O}$), 1,580 cm$^{-1}$ (benzene ring) and 1,495 cm$^{-1}$ (benzene ring). Further, when the chemical shift of proton in the nuclear magnetic resonance spectrum (in a carbon tetrachloride solution) of the compound was represented by the δ value, the signal of proton of —CH$_2$CH$_3$ group appeared at a δ of 0.9 ppm (3H), that of proton of

group appeared at a δ value of 1.2 ppm (3H), that of proton of —C(CH$_3$)$_3$ group appeared at a δ of 1.4 ppm (9H), that of proton of —CH$_2$CH$_3$ group appeared at a δ of 1.7 ppm (2H) that of proton of —CH(CH$_3$)CH$_2$CH$_3$) group appeared at a δ of 2.9 ppm (1H) and that of proton of benzene ring appeared at a δ of 7.2 ppm (4H). Therefore, the compound was identified to be t-butylperoxy 2-sec-butylphenyl carbonate.

EXAMPLE 7

[Production of t-butylperoxy 3-methylphenyl carbonate]

A reaction was carried out in the same manner as described in Example 1, except that 3-methylphenyl chloroformate was used in place of phenyl chloroformate used in Example 1, to obtain 35.2 g (yield: 73%) of a compound having a GLC purity of 93%, which was a colorless liquid at room temperature.

The resulting compound had an infrared absorption spectrum having characteristic absorption bands (in a carbon tetrachloride solution) at 1,808 cm$^{-1}$ ($v_{C=O}$), 1,780 cm$^{-1}$ ($v_{C=O}$), 1,600 cm$^{-1}$ (benzene ring) and 1,500 cm$^{-1}$ (benzene ring). Further, when the chemical shift of proton in the nuclear magnetic resonance spectrum (in a carbon tetrachloride solution) of the compound was represented by the δ value, the signal of proton of —C(CH$_3$)$_3$ group appeared at a δ of 1.4 ppm (9H), that of proton of —CH$_3$ group appeared at a δ of 2.2 ppm (3H) and that of proton of benzene ring appeared at a δ of 7.2 ppm (4H). Therefore, the compound was identified to be t-butylperoxy 3-methylphenyl carbonate.

EXAMPLE 8

[Production of t-amylperoxy 2,4-dimethylphenyl carbonate]

A reaction was carried out in the same manner as described in Example 1, except that t-amyl hydroperoxide and 2,4-dimethylphenyl chloroformate were used in place of t-butyl hydroperoxide and phenyl chloroformate used in Example 1, to obtain 35.7 g (yield: 65%) of a compound having a GLC purity of 92%, which was a colorless liquid at room temperature.

The resulting compound had an infrared absorption spectrum having characteristic absorption bands (in a carbon tetrachloride solution) at 1,808 cm$^{-1}$ ($v_{C=O}$), 1,780 cm$^{-1}$ ($v_{C=O}$). 1.60 cm$^{-1}$ (benzene ring) and 1,500 cm$^{-1}$ (benzene ring). Further, when the chemical shift of proton in the nuclear magnetic resonance spectrum (in a deuterochloroform solution) of the compound was represented by the δ value, the signal of proton of —CH$_2$CH$_3$ group appeared at a δ 1.1 ppm (3H), that of proton of —C(CH$_3$)$_2$— group appeared at a δ of 1.3 ppm (6H), that of proton of —CH$_2$CH$_3$ group appeared at a δ of 1.7 ppm (2H), that of proton of —CH$_3$ group appeared at a δ of 2.2 ppm (6H) and that of proton of benzene ring appeared at a δ of 7.2 ppm (4H). Therefore, the compound was identified to be t-amylperoxy 2,4-dimethylphenyl carbonate.

EXAMPLE 9

[Production of t-butylperoxy 4-chlorophenyl carbonate]

A reaction was carried out in the same manner as described in Example 1, except that 4, chlorophenyl chloroformate was used in place of phenyl chloroformate used in Example 1, to obtain 30.9 g (yield: 58%) of a compound having an active oxygen content of 5.99% (theoretical value: 6.54%). The compound was a white crystal and had a melting point of 39°–41° C.

The resulting compound had an infrared absorption spectrum having characteristic absorption bands (in a carbon tetrachloride solution) at 1,805 cm$^{-1}$ ($v_{C=O}$), 1,780 cm$^{-1}$ ($v_{C=O}$), 1,595 cm$^{-1}$ (benzene ring) and 1,490 cm$^{-1}$ (benzene ring). Further, when the chemical shift of proton in the nuclear magnetic resonance spectrum (in a carbon tetrachloride solution) of the compound was represented by the $\delta$ value, the signal of proton of —C(CH$_3$)$_3$ group appeared at a $\delta$ of 1.4 ppm (9H) and that of proton of benzene ring appeared at a $\delta$ of 7.2 ppm (4H, symmetrical quartet due to 4-position-substituting chlorine atom). Therefore, the compound was identified to be t-butylperoxy 4-chlorophenyl carbonate.

EXAMPLE 10

[Production of 2,5-dimethyl-2,5-di(phenoxyphenylcarbonylperoxy)-hexane]

Into a four-necked flask of 1 l capacity equipped with a thermometer and a stirrer were charged 44.6 g (0.25 mol) of 2,5-dimethylhexane-2,5-dihydroperoxide, 39.6 g (0.50 mol) of pyridine and 500 g of petroleum ether, and then a mixture of 60.6 g (0.38 mol) of phenyl chloroformate and 20 g of petroleum ether was dropwise added thereto in 30 minutes while keeping the reaction system at 5° C. under stirring. After the addition, a reaction was further continued for 2 hours, to complete the reaction. After completion of the reaction, the reaction solution was washed with 500 ml of a 5% aqueous solution of hydrochloric acid once at 5° C. for 3 minutes, with 300 ml of a 10% aqueous solution of sodium hydroxide once at 5° C. for 5 minutes and further with 500 ml of water twice, each at 5° C. for 10 minutes, and then dried with a small amount of sodium sulfate. The solvent was removed from the reaction mass to obtain 45.0 g of a crude product. The crude product was recrystallized by using methanol to obtain 10.0 g of a white crystal having a melting point of 53° C., which had an active oxygen content of 7.57% (theoretical value: 7.65%).

The resulting compound had an infrared absorption spectrum having characteristic absorption bands (in a carbon tetrachloride solution) at 1,800 cm$^{-1}$ ($v_{C=O}$), 1,780 cm$^{-1}$ ($v_{C=O}$), 1,595 cm$^{-1}$ (benzene ring) and 1,495 cm$^-$(benzene ring). Further, when the chemical shift of proton in the nuclear magnetic resonance spectrum (in a carbon tetrachloride solution) of the compound was represented by the $\delta$ value, the signal of proton of —CH$_3$ group appeared at a $\delta$ of 1.3 ppm (6H), that of proton of —CH$_2$CH$_2$— group appeared at a $\delta$ of 1.7 ppm (4H) and that of proton of benzene ring appeared at a $\delta$ of 5.2 ppm (10H). Therefore, the compound was identified to be 2,5-dimethyl-2,5di-(phenoxycarbonylperoxy)hexane.

COMPARATIVE EXAMPLES 1 AND 2

[Production of cumylperoxy phenyl carbonate]

A reaction was carried out in the same manner as described in Example 1, except that cumyl peroxide was used in place of t-butyl hydroperoxide used in Example 1. Heat was abruptly generated during the reaction, but a reaction product of cumylperoxy phenyl carbonate was not able to be isolated and identified (Comparative example 1).

A reaction was carried out in the same manner as described in Example 2, except that cumyl hydroperoxide was used in place of t-butyl hydroperoxide used in Example 2. Heat was generated abruptly during the reaction, but a reaction product of cumylperoxy phenyl carbonate was not able to be isolated and identified (Comparative example 2).

It can be seen from the results of Comparative examples 1 and 2 that, in conventional methods using alkali or tert-amine, a tert-aralkylperoxy aryl carbonate, which is included within the scope of the peroxy carbonates represented by the general formula (II) in the above described Belgian Pat. No. 660383 and corresponds to the case where R represents a tert-aralkyl group and R' represents an aryl group in the general formula (II), cannot be easily obtained.

EXAMPLES 11–19 AND REFERENCE EXAMPLES 1 AND 2

[Decomposition rate constant and half-life period of peroxy aryl carbonate]

The organic peroxides obtained in Examples 1–10 were thermally decomposed at 100° C. in a cumene solution in a peroxide concentration of 0.02 mol/l to measure the decomposition rate constant and half-life period of the organic peroxides. Further, the decomposition rate constant and half-life period of conventional polymerization initiators of t-butylperoxy isopropyl carbonate and t-butylperoxy benzoate were measured in the same manner as described above. The results are shown in Table 1 altogether as Examples 1–19 and Reference examples 1 and 2, respectively. It can be seen from Table 1 that the peroxy aryl carbonate of the present invention has substantially the same decomposition behavior as that of a conventional polymerization initiator of peroxy isopropyl carbonate.

TABLE 1

| | | Decomposition rate constant and half-life period of peroxide at 100° C. | | |
|---|---|---|---|---|
| | Peroxide | Solvent | Decomposition rate constant (1/sec) | Half-life period (hrs) |
| Example | 11 t-Butylperoxy phenyl carbonate | cumene | $1.8 \times 10^{-5}$ | 11.0 |
| | 12 t-Amylperoxy phenyl carbonate | cumene | $4.7 \times 10^{-5}$ | 4.1 |
| | 13 t-Hexylperoxy phenyl carbonate | cumene | $5.9 \times 10^{-5}$ | 3.3 |

TABLE 1-continued

Decomposition rate constant and half-life period of peroxide at 100° C.

| | | Peroxide | Solvent | Decomposition rate constant (1/sec) | Half-life period (hrs) |
|---|---|---|---|---|---|
| | 14 | t-Butylperoxy 2-isopropyl-phenyl carbonate | cumene | $3.6 \times 10^{-5}$ | 5.3 |
| | 15 | t-Butylperoxy 2-sec-butyl-phenyl carbonate | cumene | $4.1 \times 10^{-5}$ | 4.7 |
| | 16 | t-Butylperoxy 3-methylphenyl carbonate | cumene | $1.8 \times 10^{-5}$ | 11.0 |
| | 17 | t-Amylperoxy 2,4-dimethyl-phenyl carbonate | cumene | $5.0 \times 10^{-5}$ | 3.9 |
| | 18 | t-Butylperoxy 4-chlorophenyl carbonate | cumene | $1.2 \times 10^{-5}$ | 16.0 |
| | 19 | 2,5-Dimethyl-2,5-di(phenoxy-carbonylperoxy)hexane | cumene | $5.3 \times 10^{-5}$ | 3.6 |
| Reference example | 1 | t-Butylperoxy isopropyl carbonate | toluene | $1.8 \times 10^{-5}$ | 11.0 |
| | 2 | t-Butylperoxy benzoate | 4-chloro-toluene | $9.8 \times 10^{-6}$ | 20.0 |

(Polymerization by the use of peroxy carbonate)

(Polymerization by the use of peroxy carbonate)

EXAMPLES 20-24 AND COMPARATIVE EXAMPLES 3-5

[Comparison of t-butylperoxy phenyl carbonate with t-butylperoxy isopropyl carbonate in the polymerization of styrene]

t-Butylperoxy phenyl carbonate obtained in Example 1 and styrene were weighed such that the resulting styrene solution or styrene-benzene mixed solution has concentrations of t-butylperoxy phenyl carbonate and styrene shown in Table 2. Into a glass ampule was charged 5 ml of the solution and deaerated by the freeze-thaw method and then heat-sealed under vacuum. Each glass ampule was placed in a thermostat kept at 100° C. to polymerize styrene. The reaction mass was sampled every predetermined hours, and the conversion of monomer to polymer and number-average polymerization degree were measured by means of a high speed liquid chromatograph, HLC-802A, made by Toyo Soda Kogyo K.K. The conversion and number-average polymerization degree were calculated by using a calibration curve previously prepared by using a standard substance. The polymerization rate and number-average polymerization degree were measured under the conditions of conversion of 10% or less. The obtained results are shown in Table 2 as Examples 20-24.

In the same manner as described above, a conventional polymerization initiator of t-butylperoxy isopropyl carbonate and styrene were weighed such that the resulting styrene or styrene-benzene mixed solution has concentrations of t-butylperoxy isopropyl carbonate and styrene shown in Table 3. Then, in the same manners as described in Example 20, the solution was sealed into a glass ampule, and a polymerization reaction was carried out to measure the polymerization rate and number-average polymerization degree. The obtained results are shown in Table 3 as Comparative examples 3-5.

TABLE 2

Polymerization[1] of styrene at 100° C. using t-butylperoxy phenyl carbonate

| Example | [M] (mol/l) | [C] (mol/l) | Polymerization rate (mol/l/sec) | Number-average polymerization degree | $\dfrac{R_p^2}{[C][M]^2}$ |
|---|---|---|---|---|---|
| 20 | 8.0 | 0.013 | $3.2 \times 10^{-4}$ | 1,400 | $1.4 \times 10^{-7}$ |
| 21 | 8.0 | 0.025 | $3.9 \times 10^{-4}$ | 940 | $1.0 \times 10^{-7}$ |
| 22 | 7.9 | 0.050 | $5.1 \times 10^{-4}$ | 700 | $9.0 \times 10^{-8}$ |
| 23[2] | 3.7 | 0.10 | $1.9 \times 10^{-4}$ | 190 | $2.9 \times 10^{-8}$ |
| 24[2] | 1.5 | 0.10 | $4.7 \times 10^{-5}$ | 64 | $1.1 \times 10^{-8}$ |

[1][M] represents concentration of styrene, and [C] represents concentration of t-butylperoxy phenyl carbonate.
[2]Solution polymerization in benzene.

TABLE 3

Polymerization[1] of styrene at 100° C. using t-butylperoxy isopropyl carbonate

| Comparative example | [M] (mol/l) | [C] (mol/l) | Polymerization rate (mol/l/sec) | Number-average polymerization degree | $\dfrac{R_p^2}{[C][M]^2}$ |
|---|---|---|---|---|---|
| 3 | 8.0 | 0.012 | $3.8 \times 10^{-4}$ | 1,200 | $2.0 \times 10^{-7}$ |
| 4 | 8.0 | 0.025 | $5.3 \times 10^{-4}$ | 870 | $1.9 \times 10^{-7}$ |
| 5[2] | 4.7 | 0.10 | $5.7 \times 10^{-4}$ | 260 | $1.9 \times 10^{-7}$ |

[1][M] represents concentration of styrene, and [C] represents concentration of t-butylperoxy isopropyl carbonate.
[2]Solution polymerization in benzene.

It can be seen from the comparison of Examples 21 and 22 with Comparative examples 3 and 4 that the use of t-butylperoxy phenyl carbonate results in a polymer having a polymerization degree about 20% lower than that of a polymer obtained by the use of t-butylperoxy isopropyl carbonate at the same polymerization rate.

In the use of t-butylperoxy isopropyl carbonate, the value of $R_p^2/([C][M]^2)$ is substantially constant value of about $2 \times 10^{-7}$, and satisfies the above described polymerization rate formula (2). However, the use of t-butylperoxy phenyl carbonate does not satisfy the above described formula (2) and the value of $R_p^2/([C][M]^2)$ decreases with increasing of the value of [C]/[M]. This means that the peroxy aryl carbonate exhibits a peculiar polymerization behavior different from the polymerization behavior of a conventional polymerization initiator and acts on a polymerization reaction along the above described reaction formulae (3)–(5).

EXAMPLES 25–33 AND COMPARATIVE EXAMPLES 6 AND 7

[Polymerization of styrene (Polymerization rate and polymerization degree of styrene)]

A bulk polymerization of styrene was carried out at 100° C. for 120 minutes according to Example 20 by using peroxides shown in the following Table 4, each in a peroxide concentration of 0.05 mol/l, in place of t-butyperoxy phenyl carbonate of 0.013 mol/l in Example 20. The resulting conversion, number-average polymerization degree and polymerization rate of the above polymerization reactions are shown in Table 4 as Examples 25–33.

For comparison, polymerization reactions were carried out according to Example 25 by using a conventional polymerization initiators of t-butylperoxy isopropyl carbonate or t-butylperoxy benzoate. The obtained results are shown in Table 4 as Comparative examples 6 and 7 together with the results of Examples 25–33.

It can be seen from Table 4 that the use of the peroxy aryl carbonate givens a polymer having a number-average polymerization degree considerably lower than that of a polymer obtained by the use of a conventional polymerization initiator at the same polymerization rate.

are referred to as Example 34 and Comparative examples 8 and 9, respectively. The conversion curves in the polymerizations are shown in FIG. 1, and the GPC (abbreviation of gel permeation chromatography) curves of the finally obtained polymers are shown in FIG. 2.

It can be seen from the converison curve shown in FIG. 1 that the use of a conventional polymerization initiator shown in Comparative examples 8 and 9 results in an abrupt increase of the polymerization rate due to the gel effect at the latter stage of the polymerization. However, in the use of the organic peroxide shown in Example 34, the gel effect is not observed, and the regulation of polymerization is easier than that in the use of the conventional polymerization initiator.

Figure 2:
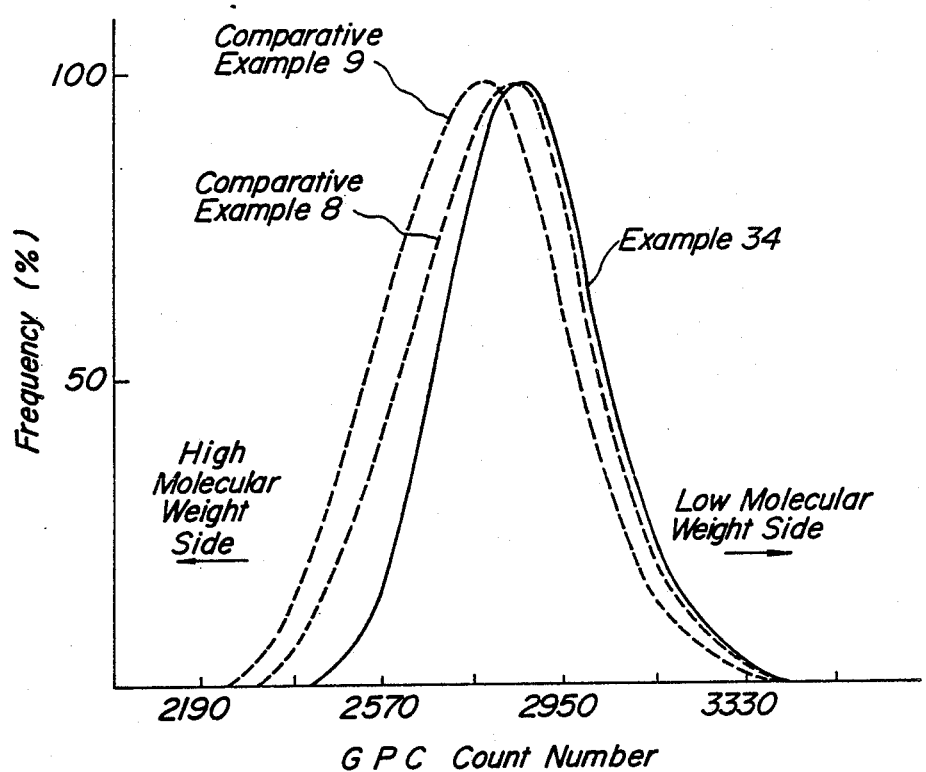

When the number-average molecular weight and the dispersion index (which is represented by the ratio of number-average molecular weight to weight-average molecular weight) of the finally obtained polymer were calculated from the GPC curve shown in FIG. 2, the number-average molecular weight and the dispersion index of the finally obtained polymer in Example 34 were found to be 90,000 and 2.4, respectively, those of the finally obtained polymer in Comparative example 8 were found to be 120,000 and 2.8 respectively and those of the finally obtained polymer in Comparative example 9 were found to be 140,000 and 3.0 respectively. These results illustrate that the polymer obtained by the use of

TABLE 4

Results of bulk polymerization of styrene at 100° C. for 120 minutes using various peroxides

| | | Peroxide | Conversion (%) | Number-average polymerization degree | Polymerization rate (%/min) |
|---|---|---|---|---|---|
| Example | 25 | t-Butylperoxy phenyl carbonate | 32 | 680 | 0.27 |
| | 26 | t-Amylperoxy phenyl carbonate | 30 | 600 | 0.25 |
| | 27 | t-Hexylperoxy phenyl carbonate | 28 | 530 | 0.23 |
| | 28 | t-Butylperoxy 2-isopropylphenyl carbonate | 35 | 660 | 0.29 |
| | 29 | t-Butylperoxy 2-sec-butylphenyl carbonate | 36 | 640 | 0.30 |
| | 30 | t-Butylperoxy 3-methylphenyl carbonate | 33 | 670 | 0.28 |
| | 31 | t-Amylperoxy 2,4-dimethylphenyl carbonate | 32 | 590 | 0.27 |
| | 32 | t-Butylperoxy 4-chlorophenyl carbonate | 28 | 720 | 0.23 |
| | 33[1] | 2,5-Dimethyl-2,5-di(phenoxycarbonylperoxy)hexane | 41 | 700 | 0.34 |
| Comparative example | 6 | t-Butylperoxy isopropyl carbonate | 55 | 730 | 0.46 |
| | 7 | t-Butylperoxy benzoate | 33 | 1,200 | 0.28 |

[1]A peroxide was used in an equivalent concentration of 0.025 mol/l.

EXAMPLE 34 AND COMPARATIVE EXAMPLES 8 AND 9

[Production of styrene resin (comparison of the organic peroxide of the present invention with other peroxides)]

Polymerizations of styrene were carried out according to Example 20 by using each of t-butylperoxy phenyl carbonate, t-butylperoxy isopropyl carbonate and t-butylperoxy benzoate in a peroxide concentration of 0.05 mol/l in place of t-butylperoxy phenyl carbonate of 0.013 mol/l in Example 20. These polymerizations t-butylperoxy phenyl carbonate has a uniform molecular weight distribution without containing a polymer having a very high molecular weight, and hence the polymer has an excellent formability.

EXAMPLE 35 AND COMPARATIVE EXAMPLES 10 AND 11

[Production of styrene resin (comparison of the organic peroxide of the present invention with other polymerization regulator)]

Polymerizations of styrene were carried out according to Comparative example 9 by adding additionally to the polymerization system t-butylperoxy phenyl carbonate, n-dodecyl mercaptan or α-methylstyrene dimer, each being kept to 0.05 mol/l concentration. These polymerizations are referred to as Example 35 and Comparative examples 10 and 11, respectively. The conversion curves in the polymerizations are shown in FIG. 3 and the GPC curves of the finally obtained polymers are shown in FIG. 4.

It can be seen from the conversion curves shown in FIG. 3 that the polymerization reaction in Example 34, which uses t-butylperoxy phenyl carbonate is shorter in the time required for completing the polymerization reaction and is more excellent in the linearity than the polymerization reactions in Comparative examples 10 and 11, which use a conventional polymerization regulator of n-dodecylmercaptan or α-methylstyrene dimer. Therefore, the use of t-butylperoxy phenyl carbonate can regulate effectively and easily a polymerization reaction.

Further, the number-average molecular weight and dispersion index of the finally obtained polymer in Example 35, which are calculated from the GPC curve shown in FIG. 4, are 74,000 and 2.4 respectively, those of the finally obtained polymer in Comparative example 10 are 60,000 and 4.8 respectively, and those of the finally obtained polymer in Comparative example 11 are 44,000 and 2.5 respectively. It can be seen from these results that the polymer obtained by the use of t-butylperoxy phenyl carbonate is equal or superior in the uniformity of the molecular weight distribution to the polymer obtained by the use of a conventional polymerization regulator. When n-dodecylmercaptan having a large chain transfer constant of 13 is used, the resulting polymer has a noticeably non-uniform molecular weight distribution, while when α-methylstyrene dimer having a small chain transfer constant of 0.3 is used, a large amount of the α-methylstyrene dimer remains in the polymer and is troublesome.

EXAMPLES 36–39 AND COMPARATIVE EXAMPLES 12–14

[Production of methyl methacrylate syrup]

Bulk polymerizations of methyl methacrylate were carried out for 90, 120, 140 or 160 minutes according to Example 20 by using a mixture of t-butylperoxy phenyl carbonate of 0.01 mol/l and methyl methacrylate in place of a mixture of t-butylperoxy phenyl carbonate of 0.013 mol/l and styrene in Example 20. The conversion in the polymerization, the number-average molecular weight and dispersion index of the finally obtained polymer, and the residual amount in percentage of initiator were measured, and the obtained results are shown in Table 5 as Examples 36–39.

For comparison, bulk polymerizations of methyl methacrylate were carried out for 30, 45 and 60 minutes according to Example 20 by using a mixture of t-butylperoxy isopropyl carbonate of 0.01 mol/l and methyl methacrylate in place of a mixture of t-butylperoxy phenyl carbonate of 0.013 mol/l and styrene in Example 20. The conversion in the polymerization, the number-average polymerization degree and distribution index of the finally obtained polymer, and the residual amount in percentage of initiator were measured, and the obtained results are shown in Table 6 as Comparative examples 12–14.

TABLE 5

Bulk polymerization of methyl methacrylate at 100° C. using t-butylperoxy phenyl carbonate

| Example | Polymerization time (min) | Conversion (%) | Number-average polymerization degree | Dispersion index | Residual amount in percentage of initiator (%) |
|---|---|---|---|---|---|
| 36 | 90 | 22 | 1,700 | 2.3 | 91 |
| 37 | 120 | 38 | 2,500 | 2.4 | 88 |
| 38 | 140 | 46 | 2,900 | 2.3 | 86 |
| 39 | 160 | 61 | 3,500 | 2.6 | 84 |

TABLE 6

Bulk polymerization of methyl methacrylate using t-butylperoxy isopropyl carbonate

| Comparative example | Polymerization time (min) | Conversion (%) | Number-average polymerization degree | Dispersion index | Residual amount in percentage of initiator (%) |
|---|---|---|---|---|---|
| 12 | 30 | 25 | 3,100 | 2.3 | 97 |
| 13 | 45 | 39 | 2,900 | 2.9 | 95 |
| 14 | 60 | 96 | 6,700 | 3.0 | 94 |

The initial polymerization rates in the polymerization reactions in Tables 5 and 6 were found to be 0.32%/min and 0.87%/min, respectively. Therefore, it is clear that the use of the peroxy aryl carbonate gives a polymer having a polymerization degree lower than that of a polymer obtained by the use of a conventional polymerization initiator at the similar polymerization rate. Moreover, Table 6 illustrates that, when a bulk polymerization of methyl methacrylate is carried out in the presence of a conventional polymerization initiator, the conversion increases abruptly from 39 to 96% and the number-average polymerization degree of the resulting polymer increases abruptly from 2,900 to 6,700 within a very short period of time of 15 minutes. On the contrary, when a bulk polymerization of methyl methacrylate is carried out in the presence of a peroxy aryl carbonate, the change of conversion is only from 38 to 61% and that of number-average polymerization degree is only from 2,500 to 3,500 even after the lapse of time of as long as 40 minutes as illustrated in Table 5. Moreover, t-butylperoxy phenyl carbonate of the present invention is lower in the residual amount in percentage than the conventional initiator of t-butylperoxy isopropyl carbonate. Therefore, the peroxy aryl carbonate of the present invention is suitable to the production of methyl methacrylate syrup, which requires a delicate control for the polymerization.

What is claimed is:

1. An organic peroxide represented by the following general formula (I)

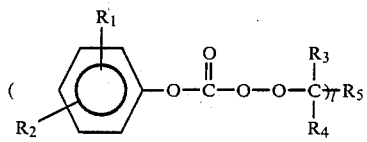 (I)

wherein l is 1, $R_1$ is a hydrogen atom, $R_2$ is 2-position-substituting isopropyl group, and $R_3$, $R_4$ and $R_5$ are methyl groups.

2. An organic peroxide represented by the following general formula (I)

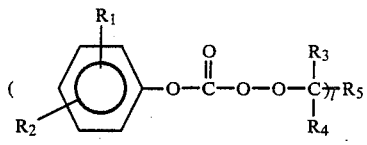 (I)

wherein l is 1, $R_1$ is a hydrogen atom, $R_2$ is 2-position-substituting sec-butyl group, and $R_3$, $R_4$ and $R_5$ are methyl groups.

3. An organic peroxide represented by the following general formula (I)

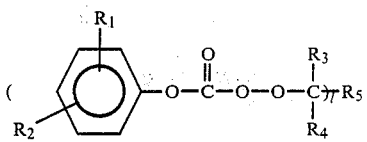 (I)

wherein l is 1, $R_1$ is a hydrogen atom, $R_2$ is 2-position-substituting chlorine atom, and $R_3$, $R_4$ and $R_5$ are methyl groups.

4. An organic peroxide represented by the following general formula (I)

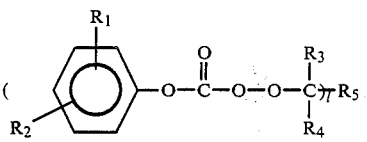 (I)

wherein l is 2, $R_1$ and $R_2$ are hydrogen atoms, $R_3$ and $R_4$ are methyl groups and $R_5$ is an ethylene group.

* * * * *